US009279055B2

(12) United States Patent
Schroeder et al.

(10) Patent No.: US 9,279,055 B2
(45) Date of Patent: Mar. 8, 2016

(54) CHROMATE-FREE CORROSION PROTECTION FOR FUEL TANKS

(75) Inventors: Sven Schroeder, Hamburg (DE); Diana Becker, Neu Wulmsdorf (DE); Jan Kuever, Stuhr (DE); Andreas Rabenstein, Bremen (DE); Martin Kaune, Bremen (DE); Yvonne Wilke, Bremen (DE); Matthias Geistbeck, Ottobrunn (DE); Carmen Gerlach, GC Rotterdam (DE); Ottmar Schramm, Drangstedt (DE); Tanja Pietzker, Bremen (DE)

(73) Assignees: Mankiewicz Gebr. & Co. GmbH & Co. KG, Hamburg (DE); Airbus Operations GmbH, Hamburg (DE)

( * ) Notice: Subject to any disclaimer, the term of this patent is extended or adjusted under 35 U.S.C. 154(b) by 728 days.

(21) Appl. No.: 12/735,553

(22) PCT Filed: Jan. 15, 2009

(86) PCT No.: PCT/DE2009/000030
§ 371 (c)(1),
(2), (4) Date: Feb. 7, 2011

(87) PCT Pub. No.: WO2009/094975
PCT Pub. Date: Aug. 6, 2009

(65) Prior Publication Data
US 2011/0124738 A1 May 26, 2011

(30) Foreign Application Priority Data

Jan. 28, 2008 (DE) .......... 10 2008 006 391

(51) Int. Cl.
C08L 63/00 (2006.01)
C09D 5/08 (2006.01)
A01N 33/12 (2006.01)
B60K 15/03 (2006.01)
C09D 163/00 (2006.01)
C09D 175/04 (2006.01)
C08G 18/48 (2006.01)
C08G 18/72 (2006.01)
C08G 18/79 (2006.01)
C08G 18/08 (2006.01)
C08K 3/32 (2006.01)

(52) U.S. Cl.
CPC .............. *C09D 5/086* (2013.01); *A01N 33/12* (2013.01); *B60K 15/03* (2013.01); *C08G 18/0866* (2013.01); *C08G 18/4804* (2013.01); *C08G 18/4887* (2013.01); *C08G 18/722* (2013.01); *C08G 18/79* (2013.01); *C09D 5/08* (2013.01); *C09D 163/00* (2013.01); *C09D 175/04* (2013.01); *B60K 2015/03046* (2013.01); *C08K 2003/328* (2013.01)

(58) Field of Classification Search
CPC ........................................................ C08L 63/00
USPC ........................................................ 523/400
See application file for complete search history.

(56) References Cited

U.S. PATENT DOCUMENTS

| 3,446,650 | A | | 5/1969 | Smith |
| 3,891,470 | A | | 6/1975 | Kotone et al. |
| 4,659,594 | A | | 4/1987 | Wu |
| 4,696,763 | A | | 9/1987 | Bentley et al. |
| 4,826,907 | A | * | 5/1989 | Murao et al. .................. 524/394 |
| 5,173,110 | A | | 12/1992 | Stovicek |
| 5,356,956 | A | * | 10/1994 | Uemae et al. ................. 523/201 |
| 5,424,355 | A | * | 6/1995 | Uemae et al. ................. 524/507 |
| 5,939,362 | A | | 8/1999 | Johnson et al. |
| 7,179,773 | B2 | | 2/2007 | Cannon, Jr. et al. |
| 2002/0098345 | A1 | * | 7/2002 | Kamo et al. .................. 428/336 |
| 2004/0213929 | A1 | * | 10/2004 | Ichikawa ............... B60K 15/03 428/34.1 |
| 2006/0008643 | A1 | * | 1/2006 | Lin et al. ....................... 428/364 |
| 2006/0151071 | A1 | | 7/2006 | Bedard et al. |
| 2006/0199917 | A1 | * | 9/2006 | Chino ........................... 525/374 |
| 2007/0093538 | A1 | | 4/2007 | Kolditz et al. |
| 2007/0269650 | A1 | | 11/2007 | Leuninger et al. |
| 2008/0045638 | A1 | * | 2/2008 | Chapman et al. ............. 524/425 |
| 2008/0206161 | A1 | * | 8/2008 | Tamarkin et al. .............. 424/45 |
| 2009/0137757 | A1 | * | 5/2009 | Imuta et al. ................... 526/127 |
| 2011/0100512 | A1 | | 5/2011 | Bedard et al. |
| 2013/0130056 | A1 | * | 5/2013 | Kimura et al. ................ 428/626 |
| 2014/0048029 | A1 | * | 2/2014 | Harle et al. ................... 123/1 A |

FOREIGN PATENT DOCUMENTS

| CA | 2 526 667 | 12/2004 |
| CA | 2 589 980 | 6/2006 |
| DE | 101 44 187 | 6/2003 |

(Continued)

OTHER PUBLICATIONS

IATA International Air Transport Association: Guidance Material on Microbiological Contamination in Aircraft Fuel Tanks; 2$^{nd}$ Edition, 2004, Ref. No. 9680-02, pp. 1-46. (Spec, p. 2).

(Continued)

*Primary Examiner* — Megan McCulley
(74) *Attorney, Agent, or Firm* — Collard & Roe, P.C.

(57) ABSTRACT

The present invention relates to a chromate-free composition, to the use thereof for corrosion protection, and to a corrosion protection coating for the inside surfaces of fuel tanks, wherein the composition comprises binding agents, hardening agents, corrosion inhibitors and quaternary ammonium compounds in a quantity of at least 0.1% by weight.

20 Claims, No Drawings

(56) References Cited

FOREIGN PATENT DOCUMENTS

| | | |
|---|---|---|
| DE | 10 2004 054 048 | 5/2006 |
| DE | 10 2005 045 129 | 3/2007 |
| EP | 1 290 943 | 3/2003 |
| EP | 1 769 680 | 4/2007 |
| GB | 133539 | 12/1918 |
| JP | 63-008462 A | 1/1984 |
| JP | 61-005069 A | 1/1986 |
| JP | 61-168675 A | 7/1986 |
| JP | 2001-49192 | 2/2001 |
| JP | 2007-244290 | 9/2007 |
| WO | WO 2004/106589 | 12/2004 |
| WO | WO 2006/061230 | 6/2006 |

OTHER PUBLICATIONS

International Search Report.
Römpp Online, Version 3.37: Definition of "Hardener" German Article with English Translation.

* cited by examiner

CHROMATE-FREE CORROSION PROTECTION FOR FUEL TANKS

CROSS REFERENCE TO RELATED APPLICATIONS

This application is the National Stage of PCT/DE2009/000030 filed on Jan. 15, 2009, which claims priority under 35 U.S.C. §119 of German Application No. 10 2008 006 391.6 filed on Jan. 28, 2008, the disclosure of which is incorporated by reference. The international application under PCT article 21(2) was not published in English.

The present invention relates to a chromate-free composition and its use for corrosion prevention and to an anticorrosive coating for fuel tanks, more particularly for their inside surfaces.

Fuels or propellants are chemical substances whose energy content is usually rendered utilizable for force generation or for the production of a drive in mechanical systems by means of combustion. Fuels are mainly employed in vehicles such as automobiles, ships, or aircraft, in which they have to be co-transported in appropriate tanks. Liquid fuels, for instance kerosene, contain, in addition to hydrocarbon atoms, also appreciable amounts of water, which water is suspended in the fuel and especially collects at the bottom of the tank. The water is also present as a thin film on the inside surface of the tank situated above the fuel level. The boundary layer between the fuel and the air also contains water. Contact between water and the surfaces or inside surfaces of the fuel tanks, which are customarily made of metal or metal alloys, generally leads to corrosion phenomena.

Corrosion is understood as meaning the detrimental and quality-decreasing change in a material, in particular a metal, starting from the surface and caused by unintentional chemical or electrochemical attack. Corrosion prevention aims at decreasing the rate of corrosion, and is divided into two large groups—active and passive corrosion prevention. Active corrosion prevention intervenes in the process of corrosion, either by treatment of the material to be protected or by counteracting the attacking (corrosive) medium. The methods of passive corrosion prevention involve keeping material to be protected isolated from the attacking medium.

Fuel tanks which are employed in aircraft are customarily made of aluminum or aluminum alloys for weight reasons. For a long time it was conventional to chromate components made of aluminum. During chromation, layers are formed on the surface of the aluminum which contain the poorly soluble hydrated oxides of aluminum and Cr(III) and Cr(VI) ions. Owing to the conversion layer or anodizing layer thus produced, the metal is protected against corrosion without need for further coating. In order to improve the corrosion resistance, a chromate-containing primer is additionally used. Chromates, however, are highly toxic and have a deleterious effect both on the environment and on humans. Meanwhile, the use of chromates is subject to strict legal regulation.

It is therefore now conventional to employ chromate-free corrosion inhibitors. Below, the term corrosion inhibitor is to be understood as meaning a substance or substance system that inhibits corrosion of a material. An anticorrosive agent is to be understood to mean a product such as a coating agent, a lacquer, a solution, or the like that contains the corrosion inhibitor or the corrosion inhibitors. Corrosion inhibitors customarily used are phosphates such as, for example, zinc phosphate, borates such as, for example, zinc borate, and silicates such as, for example, borosilicate.

The drawback of such chromate-free anticorrosive agents, however, is the unhindered microbial growth, which has hitherto been suppressed by the use of the toxic chromate ions. The corrosion inhibitors customarily employed are not only much less toxic, but polyphosphates, for example, can in additional promote microbial growth. Microorganisms, in particular bacteria and fungi such as molds and yeasts, grow on the interface between water and fuel and also on the inner tank surface to form so-called biofilms. Such biofilms can become very thick and under certain circumstances form real mats. These microbial impurities cause mechanical blockages and chocking of the return systems and fuel filters during operation of the machines that are employed for drive generation.

In addition to the mechanical effects, the microbial impurities and biofilms respectively have a corrosive effect on the inside tank surfaces. This is referred to as MIC (abbreviation for Microbiologically Induced Corrosion). The microorganisms grow adherently into the biofilm and proliferate especially on the surface thereof. Organic acids that are released as metabolic products of many of these microorganisms, lead to local acidic pHs, which in turn initiate corrosive processes on the surface of the tank interior.

In a report of the International Air Transport Association, the interaction between the microorganisms and the surface of the fuel tanks in the wings or aerofoils of aircraft is described in the following way: " . . . microorganisms are involved in a galvanic reaction, where the surface of an aluminum wing under the microorganisms serves as the anode and the microorganisms over the wing create a cathodic environment" (cf. IATA International Air Transport Association Guidance Material on Microbiological Contamination in Aircraft Fuel Tanks; 2nd edition, 2005, Ref. No. 9680-02).

In order to prevent a breakdown of the machines due to microbial contamination, in particular in aircraft during flight, the inside tank surfaces have hitherto been coated with the known chromate-containing primers in order to achieve an antimicrobial action. The residual water is also regularly removed from the tanks.

In addition, biocides are added to the kerosene itself. Although the bacterial attack takes place on or in the interfaces between kerosene and water, the overall concentration of biocide in the kerosene must be appropriately high in order to achieve an adequate action. This increases the fuel costs significantly.

Coatings having antimicrobial action are known from the field of ship's and boat's lacquers as so-called antifouling coatings. Thus U.S. Pat. No. 5,173,110 describes a composition for an antifouling coating for hulls, fishing nets and wood, which comprises an organic solution of an epoxy resin, an epoxy curing agent and a nonmetallic algicide containing a quaternary ammonium compound, which has either methyl groups and two alkyl groups or methyl groups, an alkyl group, and a benzyl group. This algicide is encapsulated in the resin and can be washed out of the composition by immersion.

This antifouling coating, however, has no kind of protective action against corrosion of metals.

It is therefore an object of the present invention to provide an improved, chromate-free coating capable, in particular, of protecting the surface of a metal from microbially induced corrosion.

This object is achieved by a composition as defined in claim 1 and the use thereof as defined in claim 11, and a coating as defined in claim 13. Preferred embodiments are the subject matter of the subclaims and the description.

The composition according to the invention comprises at least one binding agent and one or more quaternary ammonium compounds in an amount greater than 0.1% by weight based on the total weight of the composition and chromate-free corrosion inhibitors. Conventional anticorrosive agents, which are applied as a coating to a surface to be protected, are based on binder/curing agent systems, which can be water-dilutable, solvent-dilutable or solvent-free. Preferably, two-component systems are employed, which are mixed just before application to a metal surface. One component, the so-called masterbatch, contains the binder, while the other component contains the curing agent. Conventional binders are, for example, epoxy resins or hydroxy functional polymers and polyols, the reactive groups of which crosslink with the substances employed as curing agents, such as amines or isocyanates, for example, to form a solid layer.

The compounds employed for the preservation of applied and cured coating films are referred to as film preserving agents. They are especially intended to reduce or prevent the fouling of the coated surfaces by fungi and algae. Usually, fungicides and herbicides such as benzimidazoles, carbamates and dithiocarbamates, N-haloalkylthio compounds, 2-n-octyl-4-isothiazolin-3-one or halogenated diurones, for example, are employed for film preservation.

The use of quaternary amines in low concentrations as pot preservatives in liquid coating substances is known to prevent the microbial degradation of water-based binder dispersions during the period between fabrication and application of the coating composition.

However, the use of antimicrobially active compounds in combination with corrosion inhibitors for corrosion prevention of lacquered substrates such as aluminum or steel, for example, is hitherto not known. It has now been found, surprisingly, that the use of quaternary ammonium compounds together with chromate-free corrosion inhibitors prevents or suppresses microbially induced corrosion.

According to the invention, binder systems based on epoxy resins or polyurethane resins are preferably employed.

In a preferred embodiment of the present invention, the binders employed are one or more epoxy resins which are selected from the group consisting of bisphenol A resins, bisphenol F resins, phenol novolaks, cresol novolak glycidyl ethers, epoxidized cycloolefins, aromatic glycidyl compounds, N-glycidyl compounds of heterocyclics and amines, glyoxaltetraphenol tetraglycidyl ether, aliphatic glycidyl ethers, cycloaliphatic and aromatic glycidyl ethers and glycidyl esters. Of these, low viscosity and medium viscosity liquid epoxy resin types, semisolid and solid epoxy resin types and mixtures thereof can be employed.

In a particularly preferred embodiment of the invention, a mixture of bisphenol A resins and bisphenol F resins is employed. According to the invention, at least one bisphenol A resin is used to advantage which is selected from liquid bisphenol A epoxy resins having an epoxide content of from 5.10 to 5.7 mol/kg and an epoxide equivalent of from 175 to 185 g/mol, semisolid bisphenol A epoxy resins having an epoxide content of from 3.7 to 4.35 mol/kg and an epoxide equivalent of from 230 to 270 g/mol and solid bisphenol A epoxy resins having an epoxide content of from 0.16 to 2.25 mol/kg and an epoxide equivalent of from 230 to 6000 g/mol.

TABLE 1

Group of bisphenol A epoxy resins preferred according to the invention

| Type designation | Epoxide content [mol/kg] | Epoxide equivalent [g/mol] |
| --- | --- | --- |
| Liquid, low viscosity | 5.25-5.70 | 175-190 |
| 0.40-0.62 | 5.10-5.40 | 185-195 |
| 0.25-0.40 | 3.70-4.35 | 230-270 |

TABLE 1-continued

Group of bisphenol A epoxy resins preferred according to the invention

| Type designation | Epoxide content [mol/kg] | Epoxide equivalent [g/mol] |
| --- | --- | --- |
| Solid, type 1 | 1.80-2.25 | 450-550 |
| Solid, type 2 | 1.45-1.80 | 550-700 |
| Solid, type 4 | 1.05-1.25 | 800-950 |
| Solid, type 7 | 0.40-0.62 | 1600-2500 |
| Solid, type 9 | 0.25-0.40 | 2500-4000 |
| Solid, type 10 | 0.16-0.25 | 4000-6000 |
| High molecular weight | <0.05 | >20 000 |
| Phenoxy resins | <0.01 | >100 000 |

According to the invention, advantageously at least one bisphenol F epoxy resin having an epoxide content of from 5.6 to 6.1 mol/kg and an epoxide equivalent of from 158 to 175 g/mol and solid bisphenol F epoxy resins having an epoxide content of from 6 to 6.3 mol/kg and an epoxide equivalent of from 158 to 167 g/mol.

TABLE 2

Group of bisphenol F epoxy resins preferred according to the invention

| Type designation | Epoxide content [mol/kg] | Epoxide equivalent [g/mol] |
| --- | --- | --- |
| Solid | 6.0-6.3 | 158-167 |
| Liquid, low viscosity | 5.7-6.1 | 164-175 |
| Liquid, medium viscosity | 5.6-6.0 | 167-179 |

In a further preferred embodiment, the anticorrosive agent according to the invention contains, in addition to the epoxy resins, one or more suitable curing agents selected from the group consisting of the polyamines. In a particularly preferred embodiment, at least one curing agent is selected from the group consisting of the polyethylene polyamines such as, for example, ethylene diamine (EDA), diethylene triamine (DETA), triethylene tetramine (TETA), tetra-ethylene pentamine (TEPA), pentaethylene hexamine (PEHA), 1,3-pentane diamine (DAMP), 2-methylpentamethylene diamine (MPMDA), dipropylene triamine (DPTA), diethylaminopropylamine (DEAPA), trimethylhexamethylene diamine (TMD), polyoxypropylene diamines (JEFFAMINE D types) or polyoxy-propylene triamine (JEFFAMINE T types), polyether-polyamines such as, for example, polyoxyethylene polyamines (PEGDA), polyoxypropylene polyamines (PPGDA), polytetrahydrofuran polyamines (PTHFDA) or butanediol ether diamine (BDA), propylene amines such as, for example, propylene diamine (PDA), dipropylene triamine (DPTA) or N-aminopropyl cyclohexylamine (NAPCHA), alkylene diamines such as, for example, hexamethylene diamine (HMDA), trimethylhexamethylene diamine (TMD) or methylpentamethylene diamine (MPDA), cycloaliphatic amines such as, for example, tricyclododecane diamine (TCD), N-aminoethyl piperazine (NAEP), isophorone diamine (IPD) or diaminocyclohexane (DCH), aromatic amines such as, for example, diaminodiphenylmethane (DDM) or diaminodiphenylsulfone (DDS), araliphatic amines such as, for example, m-xylylene diamine (mXDA) and modifications thereof such as, for example, polyaminoamides, Mannich bases, and epoxide adducts.

According to the invention, it is preferred to use epoxy resins and amines in a molar ratio of the epoxide groups to N—H groups (EP:N—H) of from 1:0.6 to 1:1.2, more preferably from 1:0.7 to 1:1.1 and very preferably from 1:0.8 to 1:0.95.

In a further preferred embodiment of the present invention, the binders employed are one or more hydroxyl functional polymers and polyols which are crosslinked with monomeric, oligomeric, or polymeric isocyanates acting as curing agents.

Suitable isocyanates are all isocyanates customarily employed for curing coating substances such as, for example, diphenylmethane diisocyanate (MDI) and oligomers or polymers based on toluene diisocyanate (TDI), diphenylmethane diisocyanate (MDI), hexamethylene diisocyanate (HDI), isophorone diisocyanate (IPDI), 4,4'-diisocyanatodicyclohexylmethane (HMDI), m-xylylene diisocyanate (XDI), 1,6-diisocyanato-2,2,4(2,4,4)-trimethylhexane (TMDI) or tetramethylxylylene diisocyanate (TMXDI). In addition, isocyanato functional reaction products of diisocyanates with monohydric or polyhydric alcohols such as, for example, the reaction product of trimethylolpropane with an excess of toluene diisocyanate (for example that bearing the commercial name "Desmodur L" supplied by Bayer AG) are also suitable. Blocked polyisocyanates and micro-encapsulated polyisocyanates are likewise suitable.

Suitable polyols are preferably polyacrylate polyols, polyester polyols, polyether polyols, polycarbonate polyols and polycaprolactones. Aqueous dispersions of hydroxyl functional polymers based on polyacrylate, polyester, polyether, or polycarbonate are likewise suitable. Aqueous dispersions of hydroxy functional polymers based on polyurea or polyurethane are particularly suitable.

In water-dilutable coating compositions according to the invention, water-miscible polyols or polymer dispersions and isocyanates are employed, for example, in a molar ratio of the hydroxyl groups to isocyanate groups of from 1:0.8 to 1:7.5, preferably from 1:1 to 1:6 and more preferably from 1:1.5 to 1:5.

In solvent-based coating compositions according to the invention, polyols and isocyanates are employed, for example, in a molar ratio of the hydroxyl groups to isocyanate groups of from 1:0.6 to 1:2, preferably from 1:0.8 to 1:1.6 and more preferably from 1:1 to 1:1.5.

In a further preferred embodiment of the present invention, one or more quaternary ammonium compounds are employed. In order to achieve an adequate antimicrobial action of the anticorrosive agent according to the invention, at least 0.1% by weight, based on the total weight of the composition, of quaternary ammonium compounds is employed. In order to retain adequate workability and stability of the composition, not more than 5% by weight of quaternary ammonium compounds is employed. It is therefore preferred, according to the invention, to employ the ammonium compounds in a range of from 0.1 to 5% by weight and more preferably in a range of from 0.2 to 2% by weight.

Suitable quaternary ammonium compounds for the purposes of the present invention are preferably linear alkylammonium compounds of Formula I

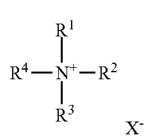

(I)

in which R1, R2, R3, and R4 are in each case an alkyl radical having from 1 to 20 carbon atoms and X is a halogen or an alkyl sulfate, imidazolium compounds of Formula II

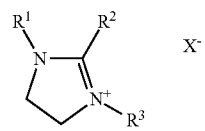

(II)

in which R1, R2 and R3 are in each case an alkyl radical having from 1 to 20 carbon atoms and X is a halogen or an alky sulfate, and pyridinium compounds of Formula III

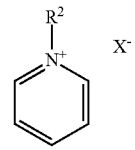

(III)

in which R2 is an alkyl radical having from 1 to 20 carbon atoms and X is a halogen or an alkyl sulfate.

Suitable quaternary ammonium compounds are, for example, benzyl-C12-18-alkyldimethyl chlorides, benzyl-C12-16-alkyldimethyl chlorides, di-C8-10-alkyldimethyl chlorides, benzyl-C12-18-alkyldimethyl salts with 1,2-benzisothiazol-3(2H)-one 1,1-dioxide, N,N'-(decane-1,10-diyldi-1(4H)-pyridyl-4-ylidene)bis(octylammonium)dichloride, 1,3-didecyl-2-methyl-1H-imidazolium chloride, 1-[1,3-bis(hydroxymethyl)-2,5-dioxoimidazolidin-4-yl]-1,3-bis-(hydroxy-methyl)urea/diazolidinyl urea, benzyl-C12-14-alkyldimethyl chlorides, C12-14-alkyl[(ethyl-phenylmethyl]dimethyl chlorides, [2-[[2-[(2-carboxyethyl)(2-hydroxyethyl)amino]ethyl]-amino]-2-oxoethyl]coco alkyl dimethyl hydroxide and the internal salts thereof, 1,3-dichloro-5-ethyl-5-methylimidazolidin-2,4-dione, reaction products of glutamic acid and N—(C12-14-alkyl)-propylene diamine, 1-(6-chloropyridin-3-ylmethyl)-nitro-imidazolidin-2-ylidene amine (commercial name: "Imidacloprid"), polymers of N-methylmethane amine (EINECS 204-697-4) with (chloromethyl)oxirane (EINECS 203-439-8)/polymeric quaternary ammonium chloride, (benzylalkyldimethyl (alkyl of C8-C22, saturated and unsaturated, and tallow alkyl, coco alkyl and soybean alkyl) chlorides, bromides or hydroxides)/BKC, (dialkyldimethyl (alkyl of C6-C18, saturated and unsaturated, and tallow alkyl, coco alkyl and soybean alkyl) chlorides, bromides or methyl sulfates)/DDAC, (alkyltrimethyl (alkyl of C8-C18, saturated and unsaturated, and tallow alkyl, coco alkyl and soybean alkyl) chlorides, bromides or methyl sulfates)/TMAC.

According to the invention, tetraalkylammonium alky sulfates, tetraalkylammonium halides, trialkylimidazolium halides, in particular dodecyldimethylethylammonium ethyl sulfate, dodecyldimethylethylammonium chloride, and dodecyldimethylethylammonium bromide, are preferred.

In a further preferred embodiment of the present invention, one or more chromate-free corrosion inhibitors are employed, which are selected from the group consisting of the phosphates such as, for example, zinc phosphates, zinc orthophosphates, calcium phosphate, dicalcium phosphate, barium phosphate, barium borophosphate, aluminum monophosphate, polyphosphate or strontium aluminum polyphosphate, the silicates such as, for example, strontium phosphosilicates, zinc phosphosilicate, calcium phosphosilicates, barium phosphosilicates, calcium borosilicate, or calcium metasilicate, the borates such as, for example, zinc borate, barium metaborate, aluminum borate, potassium borate, calcium borate, or magnesium borate, the molybdates such as, for example, calcium molybdate or zinc molybdate, organic inhibitors such as, for example, organic metal complexes or polyaniline, the oxides such as, for example, magnesium oxide or zinc oxide, and other corrosion inhibitors such as, for example, the aminophosphate salt of magnesium benzoate or ammonium benzoate.

In order to achieve an adequate corrosion-inhibiting action of the composition according to the invention, at least 0.5% by weight, based on the total weight of the composition containing corrosion inhibitors, is employed. In order to maintain an adequate workability and stability of the composition, not more than 30% by weight is employed. It is particularly preferred to employ the corrosion inhibitors in the range of from 2.5 to 15% by weight and very preferably in the range of from 5 to 10% by weight.

In a further embodiment, the composition according to the invention contains further additives familiar to the person skilled in the art, such as, for example, anti-settling agents, emulsifiers, gloss-improving agents, adhesion promoters, preservatives, delustering agents, flow improvers, rheology improvers, antifoaming agents, deaerators, wetting and dispersing agents, substrate wetting agents, and surfactants.

In a further embodiment, the composition according to the invention contains pigments and fillers as are familiar to the person skilled in the art.

In a further aspect, the object of the present invention is achieved by the use of the composition according to the invention as an anticorrosive agent, in particular as an anticorrosive agent for metals or metal alloys, preferably aluminum or aluminum alloys.

In a further aspect, the present invention relates to an antimicrobial, corrosion-inhibiting coating, which can be prepared from a composition according to the invention by applying the composition according to the invention to a surface, in particular a metal surface, and subsequently curing the resulting coating. Examples of suitable application methods include any of those familiar to the person skilled in the art, such as, for example, spraying, brushing, or rolling. Curing can take place, for example, at ambient temperature, elevated temperature or under the action of infrared radiation.

EXAMPLES

Compositions according to the present invention and comparative compositions containing conventional preservatives based on the binders of epoxy resin and polyurethane resin systems were investigated. Both water-dilutable and solvent-dilutable systems were investigated.

Example 1

Exemplary Formulations According to the Invention

Example 1a

Water-Dilutable Epoxy Resin System

Composition of the parent component:

| Ingredient | Content in % by weight |
| --- | --- |
| Mixture of epoxy resin based on bisphenol A and bisphenol F | 20 |
| Water | 20 |

-continued

| Ingredient | Content in % by weight |
| --- | --- |
| Corrosion inhibitor: zinc phosphate | 5 |
| Pigment and filler | 32 |
| Quaternary ammonium compound: dodecyldimethylethylammonium ethylsulfate | 2 |
| Additive | 11 |
| Solvent | 10 |

The curing agent employed was an epoxy/amine adduct. The mixing ratios of parent lacquer to curing agent was chosen such that the molar ratio of epoxide groups to N—H groups (EP:NH) was equal to 1:0.95.

Example 1b

Solvent-Dilutable Epoxy Resin System

Composition of the parent component:

| Ingredient | Content in % by weight |
| --- | --- |
| Bisphenol A-based epoxy resin | 35 |
| Solvent | 10 |
| Corrosion inhibitor: aluminum triphosphate | 10 |
| Pigment and filler | 40 |
| Quaternary ammonium compound: dodecyldimethylethylammonium ethylsulfate | 3 |
| Additive | 2 |

The curing agent employed was an aliphatic diamine. The mixing ratio of parent lacquer to curing agent was chosen such that the molar ratio of epoxy groups to N—H groups (EP:NH) was equal to 1:0.95.

Example 1c

Water-Dilutable Polyurethane System

Composition of the parent component:

| Ingredient | Content in % by weight |
| --- | --- |
| Aqueous, aliphatic hydroxyl group-containing polyurethane resin dispersion with a solids content of 40% based on the weight of the dispersion | 25 |
| Water | 20 |
| Additive | 2 |
| Corrosion inhibitor: zinc phosphate | 8 |
| Pigment and filler | 40 |
| Quaternary ammonium compound: dodecyldimethylethylammonium ethylsulfate | 5 |

The curing agent employed was a hydrophilized oligomeric isocyanate based on HDI and IPDI. The mixing ratio of parent lacquer to curing agent was chosen such that the molar ratio of hydroxyl groups to isocyanate groups (OH:NCO) was equal to 1:7.

Example 1d

Solvent-Dilutable Polyurethane System

Composition of the parent component:

| Ingredient | Content in % by weight |
|---|---|
| Mixture of branched polyether polyol and branched polyether/polyester polyol | 40 |
| Solvent | 10 |
| Additive | 2 |
| Corrosion inhibitor: zinc phosphate | 8 |
| Pigment and filler | 35 |
| Quaternary ammonium compound: dodecyldimethylethylammonium ethylsulfate | 5 |

The curing agent employed was an oligomeric isocyanate based on HDI. The mixing ratio of parent lacquer to curing agent was chosen such that the molar ratio of hydroxyl groups to isocyanate groups (OH:NCO) was equal to 1:1.3.

Example 2

Comparative Examples

Example 2a

Water-Dilutable Epoxy Resin System

Composition of the parent component:

| Ingredient | Content in % by weight |
|---|---|
| Mixture of epoxy resin based on bisphenol A and bisphenol F | 20 |
| Water | 20 |
| Corrosion inhibitor: zinc phosphate | 5 |
| Pigment and filler | 32 |
| Additive | 11 |
| Solvent | 10 |

The curing agent employed was an epoxy/amine adduct. The mixing ratio of parent lacquer to curing agent was chosen such that the molar ratio of epoxy groups to N—H groups (EP:NH) was equal to 1:0.95.

Example 2b

Solvent-Dilutable Epoxy Resin System

Composition of the parent component:

| Ingredient | Content in % by weight |
|---|---|
| Bisphenol A-based epoxy resin | 35 |
| Solvent | 10 |
| Corrosion inhibitor: aluminum triphosphate | 10 |
| Pigment and filler | 40 |
| Additive | 2 |

The curing agent employed was an aliphatic diamine. The mixing ratio of parent lacquer to curing agent was chosen such that the molar ratio of epoxy groups to N—H groups (EP:NH) was equal to 1:0.95.

Example 2c

Wasser-Dilutable Polyurethane System

Composition of the parent component:

| Ingredient | Content in % by weight |
|---|---|
| Aqueous, aliphatic hydroxyl-group containing polyurethane resin dispersion having a solids content of 40% based on the mass of the dispersion | 25 |
| Water | 20 |
| Additive | 2 |
| Corrosion inhibitor: zinc phosphate | 8 |
| Pigment and filler | 40 |

The curing agent employed was a hydrophilized oligomeric isocyanate based on HDI and IPDI. The mixing ratio of parent lacquer to curing agent was chosen such that the molar ratio of hydroxyl groups to isocyanate groups (OH:NCO) was equal to 1:7.

Example 2d

Solvent-Dilutable Polyurethane System

Composition of the parent component:

| Ingredient | Content in % by weight |
|---|---|
| Mixture of branched polyether polyol and branched polyether/polyester polyol | 40 |
| Solvent | 10 |
| Additive | 2 |
| Corrosion inhibitor: zinc phosphate | 8 |
| Pigment and filler | 35 |

The curing agent employed was a hydrophilized oligomeric isocyanate based on HDI and IPDI. The mixing ratio of parent lacquer to curing agent was chosen such that the molar ratio of hydroxyl groups to isocyanate groups (OH:NCO) was equal to 1:7.

Example 3

Microbial Investigation

Microorganisms were filtered off from a kerosene sample and determined taxonomically. The following fungi were identified: *Alternaria alternate, Aspergillus niger, Aspergillus versicolor, Botrytis cinerea, Cladosporium cladosporioides, Cladosporiun herbarum, Epicoccum nigrum, Paecilomyces variotii, Penicillinum brevicompactum, Penicillium expansum, Penicillium rugulosum, Penicillium spinulosum*, and *Penicilliium variabile* and also unidentified yeasts were detected. These isolates were employed in the following microbial investigations.

Example 3a

Investigations on the Antimicrobial Action

In this investigation, the test specimens coated with the corresponding exemplary formulations were exposed to (incubated with) the aforementioned fungi for a specified time under specified temperature and humidity conditions. The test specimens were exposed to the fungus spores, which were distributed on a nutrient medium making growth thereof possible. After incubation, the extent of the growth on the test specimens was determined visually, the parameters being determined according to a numerical assessment method (see Table 3).

TABLE 3

Assessment table

| | |
|---|---|
| 0 | No growth can be determined, not even under a microscope |
| 1 | Growth can barely be determined with the naked eye; but can be clearly discerned under a microscope (magnification: 50 times) |
| 2 | Slight growth, covers less than 25% of the test specimen |
| 3 | Growth covers more than 25% of the surface of the test specimen |

Procedure:

The specimens were obtained by one-sided coating of 40×50 mm sized panels of aluminum sheet (material: AA2024 clad, chromic acid anodized), using the formulations to be investigated. Under aseptic conditions, an adequate amount of full agar medium and kerosene-containing agar medium was poured into Petri dishes, such that the depth of liquid obtained was from 5 to 10 mm. The test specimens were laid individually on the solidified agar medium in the Petri dishes. An appropriate amount of the inoculation suspension, which contained spores of the above-mentioned microorganisms, was distributed on the test specimen and medium surface. The Petri dishes were closed and incubated for approximately 4 weeks at 25±1° C. and at a relative humidity of over 90% (as is usually achieved in closed Petri dishes).

Table 4 shows the results of the subsequent visual assessment of the growth of the test specimens.

Example 3b

Tank Simulation

For this, the test specimens (150×80 mm), which were in each case coated on one side with the formulations to be investigated as described in Example 3a, were placed in a glass vessel containing 2 ml of kerosene on 1 l of water. The test specimens were subsequently sprayed with a 0.1% yeast extract solution in order to simulate biological contamination. Following drying, a suspension of the aforementioned fungi was sprayed onto the surface of the test specimens. Subsequently, the test specimens were incubated in the glass container for 4 weeks.

Following incubation, the extent of growth on the test specimens was determined visually, the parameters being determined according to the aforementioned numerical assessment method (see Table 3). The results of this investigation are also summarized in Table 4.

TABLE 4

| | Test results | | | | | | | |
|---|---|---|---|---|---|---|---|---|
| | Example | | | | Comparative example | | | |
| Test | 1a | 1b | 1c | 1d | 2a | 2b | 2c | 2d |
| Antimicrobial activity (Example 3a) | 0 | 1 | 0 | 0 | 3 | 3 | 3 | 2 |

TABLE 4-continued

| | Test results | | | | | | | |
|---|---|---|---|---|---|---|---|---|
| | Example | | | | Comparative example | | | |
| Test | 1a | 1b | 1c | 1d | 2a | 2b | 2c | 2d |
| Tank simulation (Example 3b) | 0 | 0 | 0 | 0 | 3 | 2 | 2 | 3 |

The invention claimed is:

1. A coated fuel tank consisting of
   a fuel tank having an inner surface, said fuel tank made of aluminum metal or made of an aluminum metal alloy;
   a coating on said inner surface of said fuel tank; and
   said coating consisting of a composition consisting of
   at least one binding agent,
   at least one curing agent,
   at least one chromate-free corrosion inhibitor which is selected from the group consisting of zinc phosphate, aluminum triphosphate, a borate and a molybdate,
   at least one quaternary ammonium compound, in which said composition contains an amount of at least 0.1% by weight, based on the total weight of the composition, of quaternary ammonium compound; and
   said composition being chromate-free.
2. The coated fuel tank as defined in claim 1,
   wherein at least one quaternary ammonium compound is selected from the group consisting of the linear alkylammonium compounds of Formula I

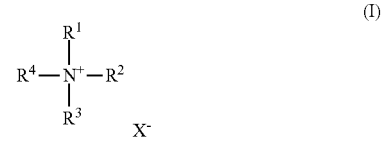

in which R1, R2, R3 and R4 each denote an alkyl group containing from 1 to 20 carbon atoms and X denotes a halogen or an alkyl sulfate,
the imidazolium compounds of Formula II

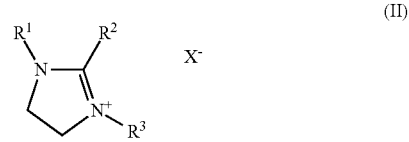

in which R1, R2, and R3 each denote an alkyl group containing from 1 to 20 carbon atoms and X is a halogen or an alkyl sulfate, and the pyridinium compounds of Formula III

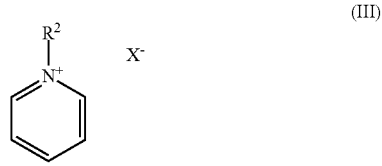

in which R2 denote an alkyl group containing from 1 to 20 carbon atoms and X is a halogen or an alkyl sulfate.

3. The coated fuel tank as defined in claim 1,
wherein said composition contains an amount of quaternary ammonium compounds of from 0.1 to 5% by weight based on the total weight of the composition.

4. The coated fuel tank as defined in claim 1,
wherein said composition contains an amount of corrosion inhibitor of from 5 to 30% by weight, based on the total weight of the composition.

5. The coated fuel tank as defined in claim 1,
wherein said binding agent is at least one polyalcohol or a hydroxy functional polymer.

6. The coated fuel tank as defined in claim 5,
wherein at least one polyalcohol is selected from the group consisting of polyacrylate polyols, polyester polyols, polyether polyols, polycarbonate polyols, and polycaprolactones.

7. The coated fuel tank as defined in claim 5,
wherein at least one hydroxy functional polymer is selected from the group consisting of polyacrylates, polyesters, polyethers, polycarbonates, polyureas, and polyurethanes.

8. The coated fuel tank as defined in claim 1,
wherein said binding agent is at least one epoxy resin.

9. The coated fuel tank as defined in claim 8,
wherein at least one epoxy resin is selected from the group consisting of bisphenol-A resins, bisphenol-F resins, phenol novolaks, cresol novolac glycidyl ether, epoxidized cycloalkenes, aromatic glycidyl compounds, N-glycidyl compounds of heterocyclic compounds and amines, glyoxaltetraphenol tetraglycidyl ether, aliphatic glycidyl ethers, cycloaliphatic glycidyl ethers, and aromatic glycidyl ethers.

10. The coated fuel tank as defined in claim 1, wherein said composition contains an amount of corrosion inhibitor of from 2.5 to 15% by weight, based on the total weight of the composition.

11. The coated fuel tank as defined in claim 10, wherein said composition contains an amount of corrosion inhibitor of from 5 to 10% by weight, based on the total weight of the composition.

12. The coated fuel tank as defined in claim 1,
wherein the corrosion inhibitor is selected from the group consisting of zinc phosphate and aluminum triphosphate.

13. The coated fuel tank as defined in claim 12,
wherein the corrosion inhibitor is zinc phosphate.

14. The coated fuel tank as defined in claim 12,
wherein the corrosion inhibitor is aluminum triphosphate.

15. The coated fuel tank as defined in claim 1,
wherein the Quaternary ammonium compound is selected from the group consisting of dodecyldimethylethylammonium ethylsulfate and dodecyldimethylethylammonium chloride.

16. A coated fuel tank consisting of
a fuel tank having an inner surface, said fuel tank made of aluminum metal or made of an aluminum metal alloy;
a coating on said inner surface of said fuel tank; and
said coating consisting of a composition consisting of
at least one binding agent,
at least one curing agent,
at least one chromate-free corrosion inhibitor and
at least one quaternary ammonium compound, in which said composition contains an amount of at least 0.1% by weight, based on the total weight of the composition, of quaternary ammonium compound; and
wherein the at least one corrosion inhibitor is selected from the group consisting of zinc phosphate, aluminum triphosphate, a borate and a molybdate; and
wherein the composition comprises a two-component system selected from the group consisting of an epoxide resin system (a) and a polyurethane system (b); system (a) having an epoxide resin as a binding agent and an amine as a curing agent and system (b) having a polyol as a binding agent and an isocyanate as a curing agent; and said composition being chromate-free.

17. The coated fuel tank as defined in claim 16,
wherein the corrosion inhibitor is selected from the group consisting of zinc phosphate and aluminum triphosphate.

18. The coated fuel tank as defined in claim 17,
wherein the corrosion inhibitor is zinc phosphate.

19. The coated fuel tank as defined in claim 17,
wherein the corrosion inhibitor is aluminum triphosphate.

20. The coated fuel tank as defined in claim 16,
wherein the Quaternary ammonium compound is selected from the group consisting of dodecyldimethylethylammonium ethylsulfate and dodecyldimethylethylammonium chloride.

* * * * *